(12) United States Patent
Hyckenberg et al.

(10) Patent No.: US 11,862,335 B2
(45) Date of Patent: Jan. 2, 2024

(54) METHOD AND SYSTEM FOR MONITORING AND CONTROLLING INSTRUMENTS

(71) Applicant: Cytiva Sweden AB, Uppsala (SE)

(72) Inventors: Key Hyckenberg, Uppsala (SE); Kjell Karlsson, Uppsala (SE); Stefan Willehadson, Uppsala (SE); Orjan Bo Grelsson, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 42 days.

(21) Appl. No.: 18/147,546

(22) Filed: Dec. 28, 2022

(65) Prior Publication Data

US 2023/0138356 A1    May 4, 2023

Related U.S. Application Data

(63) Continuation of application No. 16/497,022, filed as application No. PCT/EP2018/058019 on Mar. 28, 2018, now Pat. No. 11,568,986.

(30) Foreign Application Priority Data

Mar. 28, 2017   (GB) ...................................... 1704970

(51) Int. Cl.
*G08B 21/18*        (2006.01)
*G06K 19/077*       (2006.01)
(Continued)

(52) U.S. Cl.
CPC ........... *G16H 40/67* (2018.01); *G06F 3/0483* (2013.01); *G06F 3/04842* (2013.01);
(Continued)

(58) Field of Classification Search
CPC ... G16H 40/67; G06F 16/9558; G06F 3/0483; G06F 3/04842; H04L 67/025;
(Continued)

(56) References Cited

U.S. PATENT DOCUMENTS

| | | | |
|---|---|---|---|
| 10,089,850 B2 * | 10/2018 | Potyrailo | ........... G06K 19/0707 |
| 10,585,095 B2 | 3/2020 | Sulya | |
| 2002/0184326 A1 | 12/2002 | Thomson | |
| 2002/0198964 A1 | 12/2002 | Fukazawa et al. | |
| 2005/0080799 A1 | 4/2005 | Harnden et al. | |

(Continued)

FOREIGN PATENT DOCUMENTS

| | | |
|---|---|---|
| CN | 103973733 A | 8/2014 |
| EP | 1956760 A1 | 8/2008 |
| WO | 00/67134 A1 | 11/2000 |

OTHER PUBLICATIONS

Agham et al., Mobile and web based monitoring of patient's physiological parameters using LabVIEW, 6 pages (Year: 2014).*

(Continued)

*Primary Examiner* — Thuy Dao
(74) *Attorney, Agent, or Firm* — Eversheds Sutherland (US) LLP (57) ABSTRACT

A method, system, gateway and computer program for remote controlling and monitoring of at least one instrument, for example a bioprocessing instrument. The system can comprise: at least one instrument to be controlled and/or monitored; at least one instrument server connected to the at least one instrument, said instrument server comprising an instrument control software; at least one gateway connected to the at least one instrument server; a transferring means provided in the at least one instrument server, said transferring means being arranged to receive information from the at least one connected instrument and forward said information to the at least one gateway.

17 Claims, 3 Drawing Sheets

(51) Int. Cl.
| | |
|---|---|
| *G06F 9/445* | (2018.01) |
| *G06F 9/455* | (2018.01) |
| *G16H 40/67* | (2018.01) |
| *G06F 16/955* | (2019.01) |
| *G06F 3/0483* | (2013.01) |
| *G06F 3/04842* | (2022.01) |
| *H04L 67/025* | (2022.01) |
| *H04L 67/125* | (2022.01) |

(52) U.S. Cl.
CPC ........ *G06F 16/9558* (2019.01); *H04L 67/025* (2013.01); *H04L 67/125* (2013.01)

(58) Field of Classification Search
CPC ..... H04L 67/125; C12M 41/48; C12M 29/20; C12M 29/00; C12M 23/06; C12M 47/12; C12M 23/40; B33Y 80/00
See application file for complete search history.

(56) References Cited

U.S. PATENT DOCUMENTS

2005/0155043 A1 7/2005 Schulz et al.
2009/0099668 A1 4/2009 Lehman et al.
2015/0304398 A1 10/2015 Letca

OTHER PUBLICATIONS

PCT International Search Report and Written Opinion for PCT Application No. PCT/EP2018/058019 dated Jul. 18, 2018 (10 pages).
Great Britain Search Report for GB Application No. 1604614.6 dated Sep. 7, 2016 (4 pages).
Chinese Office Action for CN Application No. 201880035151.7, dated Jul. 5, 2021 (27 pages).
Koshatwar, et al., Remote monitoring and control of industrial parameters using embedded web server, 4 pages (2016).

* cited by examiner

METHOD AND SYSTEM FOR MONITORING AND CONTROLLING INSTRUMENTS

CROSS REFERENCE TO RELATED APPLICATIONS

This application is a continuation of U.S. application Ser. No. 16/497,022, filed on Sep. 24, 2019, which claims the priority benefit of PCT/EP2018/058019 filed on Mar. 28, 2018, which claims priority benefit of Great Britain Application No. 1704970.1 filed on Mar. 28, 2017, the entire contents of which are incorporated herein by reference.

TECHNICAL FIELD OF THE INVENTION

The present invention relates to a method and a system for remote monitoring and controlling of at least one instrument.

BACKGROUND OF THE INVENTION

Monitoring and control of analytical and bioprocess instruments, such as for example chromatography systems, filtration systems and bioreactors is usually done from an instrument server comprising a specifically designed monitoring and control program for each instrument separately.

Problems with these conventional systems are that they lack a central monitoring point. Typically large installations containing several instruments and types of instruments are monitored manually where each instrument needs a manual inspection. These inspections are of great importance since critical operations might be in action where it is of importance to know about any failure as soon as possible.

SUMMARY

An object of the invention is to provide an improved method for monitoring and controlling one or more instruments.

This object is addressed by a method for remote monitoring and controlling of at least one instrument, said method comprising the steps of:
  collecting information from the at least one instrument in at least one instrument server connected to the at least one instrument;
  forwarding the information to a gateway connected to the at least one instrument server;
  publishing the information from the instruments received in the gateway in an instrument monitoring web page using a second self-hosted web server containing a web application provided in the gateway;
  opening the instrument monitoring web page from a client connected to the gateway;
  monitoring from the client the instrument information shown in the instrument monitoring web page;
  choosing at least one of the instruments to control by selecting a hyperlink in the instrument monitoring web page;
  redirecting the instrument monitoring web page to an instrument controlling web page provided by a first self-hosted web server containing a web application provided in the instrument server;
  controlling at least one of the instruments from the client through the instrument controlling web page.

The object is also addressed in a method for providing remote control and monitoring of at least one instrument, said method comprising the steps of:
  providing a transferring means to at least one instrument server, said transferring means being arranged to receive information from at least one instrument connected to the instrument server and forward said information to a gateway which is connected to the at least one instrument server;
  providing a first self-hosted web server containing a web application in the at least one instrument server for providing possibility to control the at least one instrument via a web browser in an instrument control web page;
  providing a publishing means in the gateway, said publishing means being arranged to receive information from at least one instrument server and publish said information on an instrument monitoring web page;
  providing a second self-hosted web server containing a web application in the gateway for providing possibility to monitor the at least one instrument in the instrument monitoring web page via a web browser.

The object is also addressed by a system for remote controlling and monitoring of at least one instrument, said system comprising:
  at least one instrument to be controlled and/or monitored;
  at least one instrument server connected to the at least one instrument, said instrument server comprising an instrument control software;
  at least one gateway connected to the at least one instrument server;
  a transferring means provided in the at least one instrument server, said transferring means being arranged to receive information from the at least one connected instrument and forward said information to the at least one gateway;
  a first self-hosted web server containing a web application provided in the at least one instrument server for providing possibility to control the at least one instrument via a web browser in an instrument control web page;
  a publishing means provided in the at least one gateway, said publishing means being arranged to receive information from at least one instrument server and publish said information in an instrument monitoring web page;
  a second self-hosted web server containing a web application provided in the at least one gateway for providing possibility to monitor the at least one instrument in the instrument monitoring web page via a web browser.

The object is also addressed by a gateway provided in a system for remote controlling and monitoring of at least one instrument, said system comprising at least one instrument to be controlled and/or monitored and at least one instrument server connected to the at least one instrument said instrument server comprising an instrument control software, said gateway being connected to the at least one instrument server and comprising:
  a publishing means, said publishing means being arranged to receive information about the at least one instrument from the at least one instrument server and publish said information in an instrument monitoring web page;
  a second self-hosted web server containing a web application for providing possibility to monitor the at least one instrument in the instrument monitoring web page via a web browser.

The object is also addressed by a computer program product arranged to be provided in a system for remote controlling and monitoring of at least one instrument, said system comprising at least one instrument to be controlled and/or monitored, at least one instrument server connected to the at least one instrument and at least one gateway connected to the at least one instrument server, said computer program product comprising instructions for causing the at least one instrument server and the gateway in the system to perform the method steps of:

collecting information from the at least one instrument in the at least one instrument server;

forwarding the information to the gateway;

publishing the information from the instruments received in the gateway in an instrument monitoring web page using a second self-hosted web server containing a web application provided in the gateway;

redirecting the instrument monitoring web page to an instrument controlling web page provided by a first self-hosted web server containing a web application provided in the instrument server when a user chooses an instrument to control in the instrument monitoring web page.

Hereby many different instruments can be monitored in the same web page and from any client connected to the gateway. Furthermore the control of each instrument is easily performed from a web browser running a web application. The use of a self-hosted web server containing a web application in both the instrument server and the gateway avoids the need for updating the software in a client computer. This is due to the fact that the web application available in the web server only needs a web browser in the client computer. Any update to the web application is done in one location only and will be available in the web browser when done.

In one embodiment said transferring means and said first self-hosted web server are provided to the at least one instrument server as an application plugin and said publishing means and said second self-hosted web server are provided to the gateway as an application plugin. Hereby there is no requirement for an update of the original instrument control software which could be a great advantage in some environments where new tests and validations are required for updated software.

In one embodiment the method further comprises providing at least one hyperlink in the instrument monitoring web page, wherein said at least one hyperlink will redirect a user selecting, e.g. clicking, the hyperlink to the instrument control web page.

In one embodiment the instrument or instruments which are monitored and controlled are bioprocessing instruments.

BRIEF DESCRIPTION OF THE DRAWINGS

Further advantages and benefits of the present invention will become readily apparent to the person skilled in the art in view of the detailed description below, and the drawings, wherein.

DETAILED DESCRIPTION OF THE EMBODIMENTS

Figure 1:
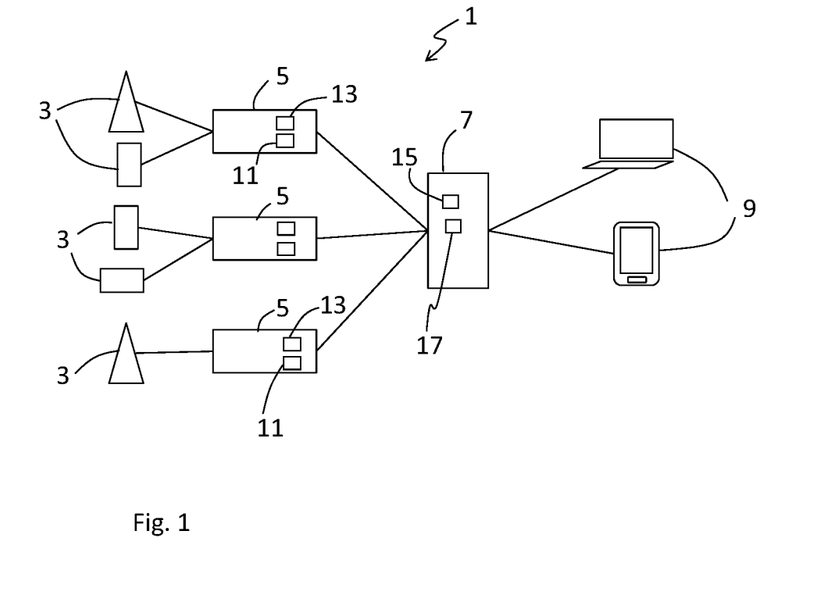
FIG. 1 shows schematically a network structure for a remote monitoring and control system.

FIG. 1 shows schematically a network structure for a system 1 for remote controlling and monitoring of at least one instrument 3 according to one embodiment of the invention. The system 1 comprises at least one instrument 3 to be controlled and/or monitored. This could be an analytical or bioprocessing instrument or a process development instrument such as for example a chromatography system, a filtration system, a bioreactor, a peptide synthesis system or an electrophoresis system. The system comprises further at least one instrument server 5 which is connected to the at least one instrument 3. More than one instrument 3 can be connected to the same instrument server 5. In the embodiment shown in FIG. 1 three instrument servers 5 are shown. Two of the instrument servers 5 are connected to two instruments 3 each and one instrument server 5 is connected to one instrument 3. This is however only an example. Any number of instruments 3 could be connected to each one of the instruments servers 5 and the system 1 can comprise any number of instrument servers 5. The at least one instrument server 5 comprises an instrument control software for controlling the instruments 3 connected to this instrument server 5. The system 1 comprises further at least one gateway 7 connected to the at least one instrument server 5. A client 9, here shown in the form of a computer and a mobile telephone having computing ability can connect to the gateway 7.

Control and/or monitoring of the instruments 3 can be performed from the clients 9.

A transferring means 11 is provided in the at least one instrument server 5. Said transferring means 11 is arranged to receive information from the at least one connected instrument 3 and forward said information to the at least one gateway 7. Furthermore a first self-hosted web server 13 containing a web application is provided in the at least one instrument server 5 for providing possibility to control the at least one instrument 3 via a web browser. An instrument control web page is provided by the at least one instrument server 5. A client 9 can access the instrument control web page through the gateway 7 which will be further explained below.

A publishing means 15 is provided in the at least one gateway 7. Said publishing means 15 is arranged to receive information about the instruments 3 from at least one connected instrument server 5 and publish said information in an instrument monitoring web page. Said publishing of information in the instrument monitoring web page is performed automatically when an instrument is connected. The gateway 7 comprises a second self-hosted web server 17 containing a web application. The second self-hosted web server provides the possibility to publish the information in a web page and provides the possibility to monitor the at least one instrument via a web browser. Hereby a client 9 connected to the gateway 7 can monitor the instruments 3 via the instrument monitoring web page.

Said transferring means 11 and said first self-hosted web server 13 are provided to the instrument server 5 as an application plugin. Herein the term plugin is intended to refer to an extension provided to already existing software and could also be called just an extension or an addon. In this invention it is an advantage to provide both the transferring means and the first self-hosted web server 13 to the instrument server 5 as a plugin because then there is no requirement for an update of the original instrument control software. In some environments, particularly in the bioprocessing field there may be requirements for new validations and tests if a software is updated and therefore a plugin is s preferred instead of updating the software since it means that no validation is necessary. The use of a self-hosted web server within the instrument server 5 furthermore avoids the need for updating the software in a client computer. Furthermore, said publishing means 15 and said second self-hosted web server 17 are provided to the gateway 7 as a plugin for the same reasons as given above.

Said system 1 comprises further at least one software hyperlink URL or the like provided in the instrument monitoring web page, wherein said at least one hyperlink will redirect a user selecting, for example by clicking, the hyperlink to the instrument control web page.

Hereby the instruments 3 can be both monitored and controlled remotely from a client 9 connected to the gateway 7. A user of the client will open the instrument monitoring web page and there all the instruments 3 connected to the system 3 will be shown in a graphical user interface dashboard. Information relating to the instruments 3 can be shown in the dashboard. Such information can be for example alerts, faults, logs, users, methods or any other type of data available in the instrument. Each instrument 3 shown in the dashboard (instrument monitoring web page) is provided with a hyperlink. When a user clicks the hyperlink the user is redirected to the instrument control web page associated with this specific instrument 3 and this specific instrument server 5 connected to the instrument 3. In the instrument control web page the user can control the instrument.

The gateway 7 is further connected via a firewall to the Internet. Thereby, a client (web browser) could connect to the gateway 7 through Internet. Such Internet connection would of course require authentication and authorization of users. In addition to this a secure connection using encryption is required in order to ensure protection of data transferred between the web server and web browser. Analysis of data retrieved from the instruments and shown in the instrument monitoring web page could in this case be provided over Internet. Furthermore comparison and statistics from many different systems like the system 1 shown in FIG. 1 could be provided over Internet.

Figure 2:
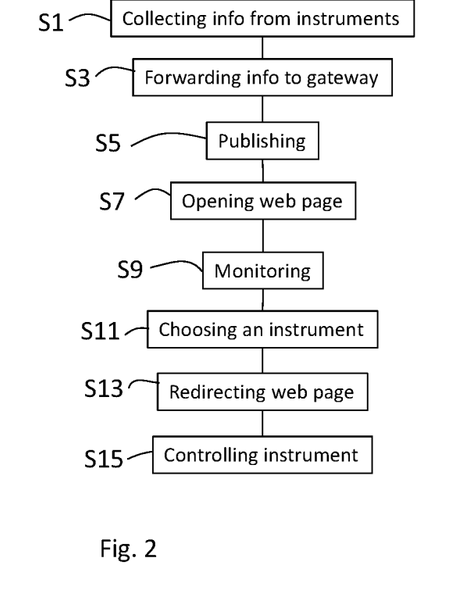
FIG. 2 is a flow chart of a method for remote monitoring and controlling of at least one instrument.

FIG. 2 is a flow chart of a method for remote monitoring and controlling of at least one instrument 3 according to one embodiment of the invention. The method comprises the steps of:

S1: Collecting information for example of the type described below, from the at least one instrument 3 in at least one instrument server 5 connected to the at least one instrument.

S3: Forwarding the information to a gateway 7 connected to the at least one instrument server 5.

S5: Publishing the information from the instruments 3 received in the gateway 7 in an instrument monitoring web page using a self-hosted web server 17 containing a web application and provided in the gateway 7.

S7: Opening the instrument monitoring web page from a client 9 connected to the gateway 7, for example connected via the Internet or a LAN.

S9: Monitoring from the client 9 the instrument information shown in the instrument monitoring web page.

S11: Choosing at least one of the instruments 3 to control by selecting an appropriate hyperlink in the instrument monitoring web page.

S13: Redirecting the instrument monitoring web page to an instrument controlling web page provided by a self-hosted web server 13 containing a web application and provided in the instrument server 5.

S15: Controlling at least one of the instruments 3 directly from the client 9 through the instrument controlling web page, for example via the Internet or a LAN.

In one embodiment the step of forwarding the information to a gateway 7 comprises forwarding information to the gateway from at least two instrument servers 5 connected to the gateway. In one embodiment the step of monitoring comprises monitoring more than one instrument in the same instrument monitoring web page. The gateway 7 can be a network node which can receive data from plural instrument servers 5 formatted according to different protocols, where the instrument servers 5 are a distributed network employing packet switching.

Figure 3:
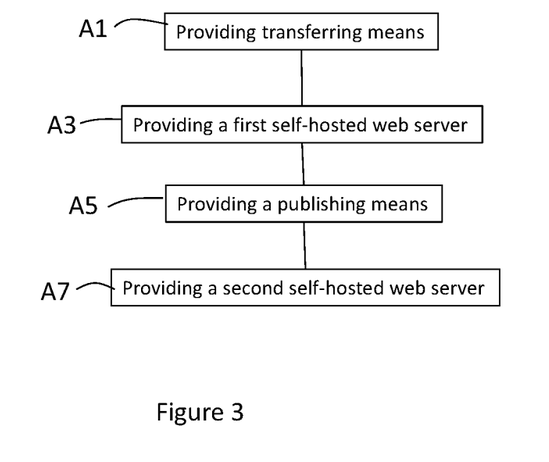
FIG. 3 is a flow chart of a method for providing remote control and monitoring of at least one instrument.

FIG. 3 is a flow chart of a method for providing remote control and monitoring of at least one instrument 3 according to one embodiment of the invention. The method comprises the steps of:

A1: Providing a transferring means 11 to at least one instrument server 5. Said transferring means 11 is arranged to receive information from at least one instrument 3 connected to the instrument server 5 and forward said information to a gateway 7 which is connected to the at least one instrument server 5.

A3: Providing a first self-hosted web server 13 containing a web application in the at least one instrument server 5 for providing possibility to control the at least one instrument 3 via a web browser in an instrument control web page.

A5: Providing a publishing means 15 in the gateway 7. Said publishing means is arranged to receive information about at least one instrument 3 from at least one instrument server 5 and publish said information on an instrument monitoring web page.

A7: Providing a second self-hosted web server 17 containing a web application in the gateway 7 for providing possibility to monitor the at least one instrument 3 via a web browser and the instrument monitoring web page.

According to one embodiment said transferring means 11 and said first self-hosted web server 13 are provided to the at least one instrument server 5 as an application plugin and said publishing means 15 and said second self-hosted web server 17 are provided to the gateway 7 as a plugin as discussed above.

In one embodiment of the invention the method further comprises providing a URL or the like hyperlink for each instrument in the instrument monitoring web page to a corresponding instrument control web page for each instrument.

The system and method according to the invention can be performed in a computer program product arranged to be provided in a system for remote controlling and monitoring of at least one instrument. Said system comprises at least one instrument to be controlled and/or monitored, at least one instrument server connected to the at least one instrument and at least one gateway connected to the at least one instrument server. Said computer program product comprises instructions for causing the at least one instrument server and the gateway in the system to perform the method steps of:

collecting information from the at least one instrument in the at least one instrument server;

forwarding the information to the gateway;

publishing the information from the instruments received in the gateway in an instrument monitoring web page using a self-hosted web server containing a web application provided in the gateway;

redirecting the instrument monitoring web page to an instrument controlling web page provided by a self-hosted web server containing a web application provided in the instrument server when a user chooses an instrument to control in the instrument monitoring web page.

The system mentioned above has particular utility for the monitoring and control of bioprocessing instruments, particularly but not exclusively of the type sold under the brand names of AKTA, and WAVE, as sold by GE Healthcare Bio-Sciences. These instruments are of the type that can be reconfigured to provide different functionality, and therefore are not necessarily performing exactly the same function all the time. Thus, remote monitoring and control is of more importance than monitoring and control of process equipment where the inputs and outputs do not change. Also, these branded instruments require provision for both breakdown maintenance and preventative maintenance, as well as replacement and supply of consumables. These branded instruments can have increased capacity or increased functionality, if ancillary components are employed, and therefore, there is a need for inventory control of such consumables and ancillary components.

Figure 4:
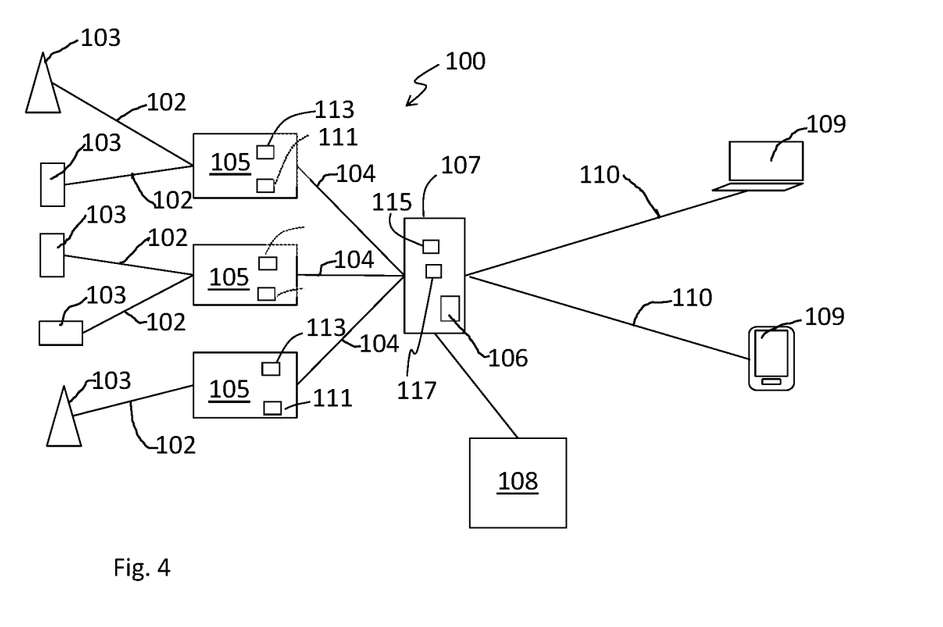
FIG. 4 shows a further embodiment of a network structure for a bioprocessing instrument monitoring and control system.

FIG. 4 shows a network system 100 similar to that shown in FIG. 1, where like features have reference numerals which include the same last two digits. The architecture of the system 100 is the same as described above. The information 102 transmitted from the instruments 103 for example an AKTA chromatography instrument or WAVE bioreactor to the instrument server 105, for the purpose of monitoring instrument performance typically includes data indicative of any one or more of:

Process run time;
Sensor data over time (curve data);
Process steps employed;
Process step progression; and
Error events, error logs and warnings.

The data is formatted at the instrument server 105 and then transmitted, for example as packet switched data 104 to the gateway 107. In order to enhance the performance of the gateway 107, for example when long-running processes are monitored, the gateway in this embodiment includes memory storage 106 to store or buffer the data 104 until it is accessed by a client 109. To further enhance the functionality of the system, two-way communication is available between an inventory server 108 and the gateway, where the inventory server is configured in a similar way to the instrument servers, such that formatted data is received from the inventory server, again accessible by the client 109. The inventory server 108 has real-time records of ancillary equipment and consumables, which can be physically located in the vicinity of the instruments, or more remotely. The inventory server hosts a web application allowing client control for the purposes of ordering and reservation of ancillary components and consumables.

Instrument data 110, which can include inventory data is transmitted to the client again optionally via packet switched data across the Internet or via a LAN. That data can be data relating to individual instrument, or collated data, for example indicative of errors or warnings only from all instruments.

The instrument data 102 transmitted to the instrument server may also be used for the purpose of instrument maintenance (preventative or breakdown maintenance), and may include:

Error events, error logs and warnings;
Instrument run time;
Run time for instrument critical parts, as such valve cycles, UV lamp burn time; pump strokes;
Power consumption which is out of limit; and
Excessive consumption of consumables.

Again such data can be formatted at the instrument servers 105 for onward transmission to the gateway 107, stored if necessary at memory 106, and accessed by a client 109. Access to inventory data from the inventory server 108 allows unexpected maintenance to be scheduled via the control steps mentioned above, i.e. where the client can access instrument control software via a web-based application hosted at the instrument server, if necessary relying on the monitoring data and inventory data mentioned above, for example by reserving ancillary components from a physical inventory to supplement or replace the monitored instrument. Consumable items too can be reserved via the client 109.

Control of the instruments 103 via a client 109 can be directly via each instrument server, the client being directed via a hyperlink to the appropriate server, via conventional security software. Such control can include control data sent by the client for the purpose of:

Selecting an appropriate process routine;
Including or omitting steps in a process routine;
Pausing a routine for adding or removing ancillary equipment;
Pausing a routine to replace a malfunctioning or defective part;
Pausing a routine for replacing or adding a consumable; and/or
Starting or stopping the instrument.

The examples given above in relation to bioprocessing instruments are examples only, and other instruments can be controlled and monitored using this system. Nevertheless the advantages of monitoring and control according to the system described allow for efficient and fast control of multiple instruments which are functionally adaptable and disparate in function and/or physical location, so can be adapted for use across multiple industrial applications.

The invention claimed is:

1. A method for remote monitoring and controlling of at least one bioprocessing instrument, said method comprising the steps of:

collecting information from the at least one bioprocessing instrument in at least one instrument server connected to the at least one bioprocessing instrument;

forwarding the information to a gateway connected to the at least one instrument server;

publishing the information from the instruments received in the gateway in an instrument monitoring web page using a second self-hosted web server containing a web application provided in the gateway;

opening the instrument monitoring web page from a client connected to the gateway;

monitoring from the client the instrument information shown in the instrument monitoring web page;

choosing at least one of the bioprocessing instruments to control by selecting a hyperlink in the instrument monitoring web page;

redirecting the instrument monitoring web page to an instrument controlling web page provided by a first self-hosted web server containing a web application provided in the instrument server; and controlling at least one of the instruments from the client through the instrument controlling web page.

2. The method according to claim 1, wherein the step of forwarding the information to a gateway comprises forwarding information to the gateway from at least two instrument servers connected to the gateway.

3. The method according to claim 1, wherein the step of monitoring comprises monitoring more than one instrument in the same instrument monitoring web page.

4. The method according to claim 1, wherein said at least one bioprocessing instrument comprises plural instruments, said instruments optionally requiring consumables for performing said bioprocessing.

5. A method for providing remote control and monitoring of at least one bioprocessing instrument, said method comprising the steps of:
provㅇiding transferring software to at least one instrument server, said transferring software being arranged to receive information from at least one bioproces sing instrument connected to the instrument server and forward said information to a gateway which is connected to the at least one instrument server;
providing a first self-hosted web server containing a web application in the at least one instrument server for providing possibility to control the at least one bioprocessing instrument via a web browser in an instrument control web page;
providing publishing software in the gateway, said publishing software being arranged to receive information from at least one instrument server and publish said information on an instrument monitoring web page; and
providing a second self-hosted web server containing a web application in the gateway for providing possibility to monitor the at least one bioprocessing instrument in the instrument monitoring web page via a web browser.

6. The method according to claim 5, wherein said transferring software and said first self-hosted web server are provided to the at least one instrument server as a plugin and said publishing software and said second self-hosted web server are provided to the gateway as a plugin.

7. The method according to claim 5, further comprising providing a hyperlink for each instrument in the instrument monitoring web page to a corresponding instrument control web page for each instrument.

8. A system for remote controlling and monitoring of at least one bioprocessing instrument, said system comprising:
at least one bioprocessing instrument to be controlled and/or monitored;
at least one instrument server connected to the at least one bioproces sing instrument, said instrument server comprising an instrument control software;
at least one gateway connected to the at least one instrument server;
transferring software provided in the at least one instrument server, said transferring software being arranged to receive information from the at least one connected bioprocessing instrument and forward said information to the at least one gateway;
a first self-hosted web server containing a web application provided in the at least one instrument server for providing possibility to control the at least one bioprocessing instrument via a web browser in an instrument control web page;
publishing software provided in the at least one gateway, said publishing software being arranged to receive information from at least one instrument server and publish said information in an instrument monitoring web page; and
a second self-hosted web server containing a web application provided in the at least one gateway for providing possibility to monitor the at least one bioprocessing instrument in the instrument monitoring web page via a web browser.

9. The system according to claim 8, wherein said transferring software and said first self-hosted web server are provided to the instrument server as a plugin and said publishing software and said second self-hosted web server are provided to the gateway as a plugin.

10. The system according to claim 8, further comprising at least one analytical instrument or a process development instrument.

11. The system according to claim 8, wherein said at least one bioprocessing instrument is a chromatography system, a filtration system, a bioreactor, a peptide synthesis system or an electrophoresis system.

12. The system according to claim 8, further comprising at least one hyperlink provided in the instrument monitoring web page, wherein said at least one hyperlink will redirect a user selecting the hyperlink to the instrument control web page.

13. The system according to claim 8, wherein said at least one bioprocessing instrument comprises plural instruments, said instruments optionally requiring consumables for performing said bioprocessing.

14. A gateway provided in a system for remote controlling and monitoring of at least one bioprocessing instrument, said system comprising at least one bioprocessing instrument to be controlled and/or monitored and at least one instrument server connected to the at least one bioprocessing instrument, said instrument server comprising an instrument control software, said gateway being connected to the at least one instrument server and comprising:
publishing software, said publishing software being arranged to receive information about the at least one bioprocessing instrument from the at least one instrument server and publish said information in an instrument monitoring web page; and
a second self-hosted web server containing a web application for providing possibility to monitor the at least one bioprocessing instrument in the instrument monitoring web page via a web browser.

15. The gateway according to claim 14, wherein said at least one bioprocessing instrument comprises plural instruments, said instruments optionally requiring consumables for performing said bioprocessing.

16. A computer program product arranged to be provided in a system for remote controlling and monitoring of at least one bioproces sing instrument, said system comprising at least one bioprocessing instrument to be controlled and/or monitored, at least one instrument server connected to the at least one bioproces sing instrument and at least one gateway connected to the at least one instrument server, said computer program product comprising instructions for causing the at least one instrument server and the gateway in the system to perform the method steps of:
collecting information from the at least one bioprocessing instrument in the at least one instrument server;
forwarding the information to the gateway;
publishing the information from the instruments received in the gateway in an instrument monitoring web page using a second self-hosted web server containing a web application provided in the gateway; and
redirecting the instrument monitoring web page to an instrument controlling web page provided by a first self-hosted web server containing a web application provided in the instrument server when a user chooses an instrument to control in the instrument monitoring web page.

17. The computer program product according to claim 16, wherein said at least one bioprocessing instrument comprises plural instruments requiring consumables for performing said bioprocessing.

* * * * *